United States Patent [19]

Krause et al.

[11] Patent Number: 4,726,911

[45] Date of Patent: Feb. 23, 1988

[54] HETEROCYCLIC COMPOUNDS

[75] Inventors: Joachim Krause, Dieburg; Peter Fuss, Mühltal-Traisa; Reinhard Hittich, Modautal; Bernhard Scheuble, Alsbach, all of Fed. Rep. of Germany

[73] Assignee: Merck Patent Gesellschaft Mit Beschrankter Haftung, Darmstadt, Fed. Rep. of Germany

[21] Appl. No.: 788,377

[22] Filed: Oct. 17, 1985

[30] Foreign Application Priority Data

Oct. 17, 1984 [DE] Fed. Rep. of Germany ....... 3437935

[51] Int. Cl.$^4$ ................. C07D 319/06; C07D 339/08; G02F 1/13; C09K 19/34
[52] U.S. Cl. ............................. 252/299.61; 544/238; 544/335; 544/336; 546/208; 546/268; 549/20; 549/21; 549/22; 549/369; 549/370; 549/372; 549/373; 549/374; 350/350 R
[58] Field of Search ............. 549/20, 21, 22, 369, 549/370, 372, 373, 374; 546/208, 268; 544/238, 335, 336; 252/299.61

[56] References Cited

U.S. PATENT DOCUMENTS

| | | |
|---|---|---|
| 3,676,500 | 7/1972 | Mantell et al. . |
| 4,298,528 | 11/1981 | Sethofer . |
| 4,510,069 | 4/1985 | Eidenschink et al. ......... 252/299.61 |

FOREIGN PATENT DOCUMENTS

| | | | |
|---|---|---|---|
| 107668 | 1/1985 | European Pat. Off. ....... 252/299.61 |
| 3405914 | 8/1985 | Fed. Rep. of Germany ........ 549/22 |
| 1545954 | 5/1979 | United Kingdom . |

OTHER PUBLICATIONS

Vorbrodt et al, Mol. Cryst. Liq. Cryst., 1985, vol. 123, pp. 137–141.

*Primary Examiner*—Robert T. Bond
*Attorney, Agent, or Firm*—Millen & White

[57] ABSTRACT

Compounds of the formula I $$R^1-A^1-Z^1-A^2-R^2 \qquad \text{I}$$

wherein $R^1$ and $R^2$ are each an alkyl group having 1–10 C atoms, in which one or two non-adjacent $CH_2$ groups can also be replaced by O atoms and/or CO groups and/or —OCO— groups and/or —COO— groups and/or —CH=CH— groups, or are F, Cl, Br, CN or $R^3-A^3-Z^2-$, $A^1$ is —A—, —$A^4$—A— or —A—$A^4$—, A is a 1,3-dioxane-2,5-diyl or 1,3-dithiane-2,5-diyl group which is monosubstituted or polysubstituted in the 2-position and/or 4-position by alkyl each having 1–10 C atoms and/or in the 5-position by alkyl, alkoxy, fluorinated alkyl or fluorinated alkoxy each having 1–5 C atoms, or by F, Cl, Br or CN, $A^2$, $A^3$ and $A^4$ each are 1,3-dithiane-2,5-diyl, piperidine-1,4-diyl, 1,4-bicyclo[2,2,2]octylene, decahydronaphthalene-2,6-diyl, 1,2,3,4-tetrahydronaphthalene-2,6-diyl, 1,4-phenylene, 1,4-phenylene which is substituted by one or two F and/or Cl atoms and/or $CH_3$ groups and/or CN groups and in which one or two CH groups can also be replaced by N atoms, or 1,4-cyclohexylene in which one or two non-adjacent $CH_2$ groups can also be replaced by O atoms, $Z^1$ and $Z^2$ each are —CO—O—, —O—CO—, —$CH_2CH_2$—, —$OCH_2$—, —$CH_2O$— or a single bond, and $R^3$ is H, an alkyl group having 1–10 C atoms, in which one or two non-adjacent $CH_2$ groups can also be replaced by O atoms and/or —CH=CH— groups, or is F, Cl, Br or CN, can be used as components of liquid-crystalline phases.

23 Claims, No Drawings

HETEROCYCLIC COMPOUNDS

BACKGROUND OF THE INVENTION

This invention relates to novel compounds containing substituted 1,3-dithiane-2,5-diyl or 1,3-dioxane-2,5-diyl groups.

Similar compounds have been disclosed, for example, by U.S. Pat. No. 4,298,528. However, in contrast to the present compounds, those listed therein do not contain any trisubstituted ring structures.

SUMMARY OF THE INVENTION

It is an object of this invention to provide novel stable liquid-crystalline or mesogenic compounds which are suitable for use as components of liquid-crystalline phases.

Upon further study of the specification and appended claims, further objects and advantages of this invention will become apparent to those skilled in the art.

These objects have been achieved by providing novel compounds of the formula I

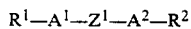    I wherein $R^1$ and $R^2$ are each an alkyl group having 1–10 C atoms, in which one or two non-adjacent $CH_2$ groups can also be replaced by O atoms and/or CO groups and/or —OCO— groups and/or —COO— groups and/or —CH=CH— groups, or are F, Cl, Br, CN or $R^3$—$A^3$—$Z^2$—, $A^1$ is —A—, —$A^4$—A— or —A—$A^4$—, A is a 1,3-dioxane-2,5-diyl or 1,3-dithiane-2,5-diyl group which is monosubstituted or polysubstituted in the 2-position and/or 4-position by alkyl each having 1–10 C atoms and/or in the 5-position by alkyl, alkoxy, fluorinated alkyl or fluorinated alkoxy each having 1–5 C atoms, or by F, Cl, Br or CN, $A^2$, $A^3$ and $A^4$ each are 1,3-dithiane-2,5-diyl, piperidine-1,4-diyl, 1,4-bicyclo[2,2,2]octylene, decahydronaphthalene-2,6-diyl, 1,2,3,4-tetrahydronaphthalene-2,6-diyl, 1,4-phenylene, 1,4-phenylene which is substituted by one or two F and/or Cl atoms and/or $CH_3$ groups and/or CN groups and in which one or two CH groups can also be replaced by N atoms, or 1,4-cyclohexylene in which one or two non-adjacent $CH_2$ groups can also be replaced by O atoms, $Z^1$ and $Z^2$ each are —CO—O—, —O—CO—, —$CH_2CH_2$—, —$OCH_2$—, —$CH_2O$— or a single bond, and $R^3$ is H, an alkyl group having 1–10 C atoms, in which one or two non-adjacent $CH_2$ groups can also be replaced by O atoms and/or —CH=CH— groups, or is F, Cl, Br and CN.

For the sake of simplicity, Ph in the text which follows represents a 1,4-phenylene group which can be unsubstituted or also substituted by one or two F and/or Cl atoms and/or $CH_3$ groups and/or CN groups, Cy represents a 1,4-cyclohexylene group and Bi represents a bicyclo[2,2,2]octylene group.

DETAILED DISCUSSION

In the same way as similar compounds, the compounds of the formula I can be used as components of liquid-crystalline phases, in particular for displays based on the principle of the twisted cell, the guest/host effect, the effect of the deformation of aligned phases, the 2-frequency method or the effect of dynamic scattering.

It has been found that the compounds of the formula I are outstandingly suitable as components of liquid-crystalline phases. Especially by means of these components, stable liquid-crystalline phases with a pronounced negative or positive dielectric anisotropy and hence a small threshold or control voltage for electro-optical effects, with a very small optical anisotropy and comparatively low viscosity can be prepared.

The provision of the compounds of the formula I also considerably broadens quite generally the range of liquid-crystalline substances which are suitable under various technological aspects for the preparation of nematic mixtures.

The compounds of the formula I have a wide range of application. Depending on the choice of the substituents, these compounds can be used as base materials, of which liquid-crystalline phases are predominantly composed; however, compounds of the formula I can also be added to liquid-crystalline base materials from other classes of compounds, for example in order to exert a significant influence on the dielectric and/or optical anisotropy of such a dielectric. The compounds of the formula I are also suitable as intermediates for the preparation of other substances which can be used as constituents of liquid-crystalline dielectrics.

In the pure state, the compounds of the formula I are colorless and form liquid-crystalline mesophases in a temperature range which is favorable for electro-optical use. They are very stable chemically, thermally and towards light. They are polar substances in which highly polar additives, such as conductive salts and dichroic dyes are readily soluble The invention thus relates to compounds of the formula I and to a process for the preparation of compounds of the formula I, which process is characterized in that a corresponding aldehyde or a corresponding ketone is reacted with a corresponding diol or dithiol, or that, for the preparation of esters of the formula I (wherein $Z^1$ and/or $Z^2$ are —CO—O— or —O—CO— and/or $R^1$ and/or $R^2$ are an alkyl group in which one $CH_2$ group is replaced by —O—CO— or —CO—O—), a corresponding carboxylic acid or a reactive derivative thereof is reacted with a corresponding alcohol or a reactive derivative thereof, or that, for the preparation of nitriles of the formula I (wherein $R^1$ and/or $R^2$ and/or $R^3$ are CN and/or A is a 1,3-dioxane-2,5-diyl or 1,3-dithiane-2,5-diyl group substituted in the 5-position by CN), a corresponding carboxamide is dehydrated or a corresponding carboxylic acid halide is reacted with sulfamide.

The invention also relates to the use of the compounds of the formula I as components of liquid-crystalline phases. In addition, the invention relates to liquid-crystalline phases containing at least one compound of the formula I and to liquid crystal display elements, in particular electro-optical display elements, which contain such phases.

Above and below, $R^1$, $R^2$, $R^3$, $A^1$, $A^2$, $A^3$, $A^4$, A, $Z^1$ and $Z^2$ have the meanings given, unless explicitly noted otherwise.

Accordingly, the compounds of the formula I comprise especially compounds of the part formulae Ia and Ib (with two rings)

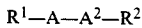    Ia $R^1$—A—$Z^1$—$A^2$—$R^2$     Ib

Ic to Ii (with three rings)

$R^1$—$A^4$—A—$A^2$—$R^2$     Ic $R^1$—A—$A^4$—$A^2$—$R^2$     Id $R^1$—$A^4$—A—$Z^1$—$A^2$—$R^2$     Ie $R^1$—A—$A^4$—$A^1$—$A^2$—$R^2$     If $R^1$—A—$Z^1$—$A^2$—$A^3$—$R^3$     Ig $R^3$—$A^3$—$Z^2$—A—$Z^1$—$A^2$—$R^2$     Ih $R^1$—A—$Z^1$—$A^2$—$Z^2$—$A^3$—$R^3$     Ii and Ij to It (with four rings)

$R^1$—$A^4$—A—$A^2$—$A^3$—$R^3$     Ij $R^1$—A—$A^4$—$A^2$—$A^3$—$R^3$     Ik $R^3$—$A^3$—$Z^2$—$A^4$—A—$A^2$—$R^2$     Il $R^3$—$A^3$—$A^4$—A—$Z^1$—$A^2$—$R^2$     Im $R^1$—A—$A^4$—$A^2$—$Z^2$—$A^3$—$R^3$     In $R^1$—A—$A^4$—$Z^1$—$A^2$—$A^3$—$R^3$     Io $R^1$—$A^4$—A—$Z^1$—$A^2$—$A^3$—$R^3$     Ip $R^1$—$A^4$—A—$Z^1$—$A^2$—$Z^2$—$A^3$—$R^3$     Iq $R^1$—A—$A^4$—$Z^1$—$A^2$—$Z^2$—$A^3$—$R^3$     Ir $R^3$—$A^3$—$Z^2$—$A^4$—A—$Z^1$—$A^2$—$R^2$     Is $R^3$—$A^3$—$Z^2$—A—$A^4$—$Z^1$—$A^2$—$R^2$     It

Those of the formulae Ia, Ib, Ic, Id, Ie, If, Ig, Ij and Ik are particularly preferred among these.

The preferred compounds of the formula Ia comprise those of the part formulae Ia1 to Ia3:

$R^1$—A—Ph—$R^2$     Ia1

$R^1$—A—Cy—$R^2$     Ia2

$R^1$—A—Bi—$R^2$     Ia3

Those of the part formulae Ia1 and Ia2 are particularly preferred among these.

The preferred compounds of the formula Ib comprise those of the part formulae Ib1 to Ib3:

$R^1$—A—$Z^1$—Ph—$R^2$     Ib1

$R^1$—A—$Z^1$—Cy—$R^2$     Ib2

$R^1$—A—$Z^1$—Bi—$R^2$     Ib3

Those of the part formulae Ib1 and Ib2, in particular those in which $Z^1$ is —CO—O—, —O—CO— or —CH$_2$CH$_2$—, are particularly preferred among these.

The preferred compounds of the formula Ic comprise those of the part formulae Ic1 and Ic2:

$R^1$—Cy—A—Cy—$R^2$     Ic1

$R^1$—Cy—A—Ph—$R^2$     Ic2

The preferred compounds of the formula Id comprise those of the part formulae Id1 to Id4:

$R^1$—A—Cy—Cy—$R^2$     Id1

$R^1$—A—Ph—Ph—$R^2$     Id2

$R^1$—A—Ph—Cy—$R^2$     Id3

$R^1$—A—Cy—Ph—$R^2$     Id4

The preferred compounds of the formula Ie comprise those of the part formulae Ie1 to Ie3:

$R^1$—Cy—A—$Z^1$—Cy—$R^2$     Ie1

$R^1$—Cy—A—$Z^1$—Ph—$R^2$     Ie2

$R^1$—Ph—A—$Z^1$—Cy—$R^2$     Ie3

Those of the part formula Ie1, in particular those in which $Z^1$ is —CO—O—, —O—CO— or —CH$_2$CH$_2$—, are particularly preferred among these.

The preferred compounds of the formula If comprise those of the part formulae If1 to If4:

$R^1$—A—Cy—$Z^1$—Cy—$R^2$     If1

$R^1$—A—Ph—$Z^1$—Ph—$R^2$     If2

$R^1$—A—Ph—$Z^1$—Cy—$R^2$     If3

$R^1$—A—Cy—$Z^1$—Ph—$R^2$     If4

Those of the part formulae If1, If2 and If3, in particular those in which $Z^1$ is —CO—O—, —O—CO— or —CH$_2$CH$_2$—, in particular —CO—O—, are particularly preferred among these.

The preferred compounds of the formula Ig comprise those of the part formulae Ig1 and Ig2:

$R^1$—A—$Z^1$—Cy—Cy—$R^3$     Ig1

$R^1$—A—$Z^1$—Ph—Cy—$R^2$     Ig2

Those in which $Z^1$ is —O—CO—, —CO—O— or CH$_2$CH$_2$— are particularly preferred among these.

The preferred compounds of the formula Ij comprise those of the part formulae Ij1 and Ij2:

$R^1$—Cy—A—Ph—Ph—$R^3$     Ij1

$R^1$—Cy—A—Ph—Cy—$R^3$     Ij2

The preferred compounds of the formula Ik comprise those of the part formulae Ik1 and Ik2:

$R^1$—A—Ph—Ph—Cy—$R^3$     Ik1

$R^1$—A—Ph—Cy—Cy—$R^3$     Ik2

In the compounds of the formulae above and below, $R^1$, $R^2$ and $R^3$ are preferably alkyl, and also an alkoxy or another oxaalkyl group.

Those compounds of the formulae above and below are also preferred in which one of the radicals $R^1$, $R^2$ or $R^3$ is —CO—alkyl, —O—CO—alkyl, —CO—O—alkyl or CN.

In the preferred compounds of the formulae above and below, the alkyl radicals, in which one CH2 group can also be replaced by an O atom (alkoxy or oxaalkyl), can be straight-chain or branched. Preferably, they are straight-chain, have 2, 3, 4, 5, 6 or 7 C atoms and accordingly are preferably ethyl, propyl, butyl, pentyl, hexyl, heptyl, ethoxy, propoxy, butoxy, pentoxy, hexoxy, heptoxy, 2-oxapropyl (=methoxymethyl), 2-(=ethoxymethyl) or 3-oxabutyl (=2-methoxyethyl), 2-, 3- or 4-oxapentyl, 2-, 3-, 4- or 5-oxahexyl, 2-, 3-, 4-, 5- or 6-oxaheptyl, and also methyl, octyl, nonyl, methoxy, octoxy or nonoxy.

$A^2$, $A^3$ and $A^4$ are preferably Cy or Ph particularly preferred are unsubstituted 1,4-phenylene or trans-1,4-cyclohexylene groups. $Z^1$ and $Z^2$ are preferably single bonds, or less preferably —O—CO—, —CO—O— or —CH2CH2—groups.

A is preferably a group selected from the formulae (A) to (F)

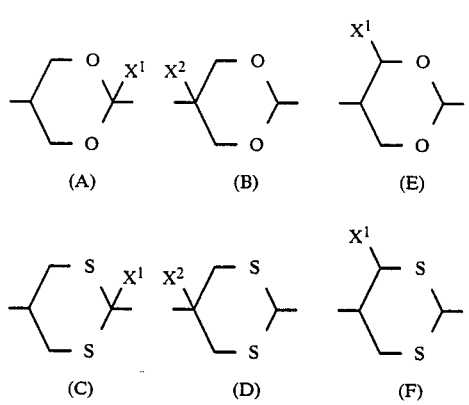

(A)  (B)  (E)

(C)  (D)  (F)

in which $X^1$ preferably is straight-chain alkyl having 1-5 C atoms and $X^2$ preferably is straight-chain alkyl or alkoxy each having 1-5 C atoms, or is F, Cl or CN.

CN—, CH3— or CH3O— groups are particularly preferred. A also comprises the mirror images of the formulae (A) to (F). The groups (A) with $X_1$=CH3 and (B) with $X^2$=CN are particularly preferred.

Compounds of the formulae above and below with branched wing groups $R^1$, $R^2$ and/or $R^3$ can sometimes be important because of their higher solubility in the usual liquid-crystalline base materials, and in particular as chiral doping substances if they are optically active. Branched groups of this type as a rule do not contain more than one chain branching.

Preferred branched radicals $R^1$ and $R^2$ are isopropyl, 2-butyl (=1-methylpropyl), isobutyl (=2-methylpropyl), 2-methylbutyl, isopentyl (=3-methylbutyl), 2-methylpentyl, 3-methylpentyl, 2-ethylhexyl, 2-propylpentyl, isopropoxy, 2-methylpropoxy, 2-methylbutoxy, 3-methylutoxy, 2-methylpentoxy, 3-methylpentoxy, 2-ethylhexoxy, 1-methylhexoxy, 1-methylheptoxy, 2-oxa-3-methylbutyl and 3-oxa-4-methylpentyl.

Among the compounds of the formula I as well as Ia to It, those are preferred in which at least one of the radicals contained therein has one of the indicated preferred meanings. Particularly preferred smaller groups of compounds are those of the formulae I1 to I10.

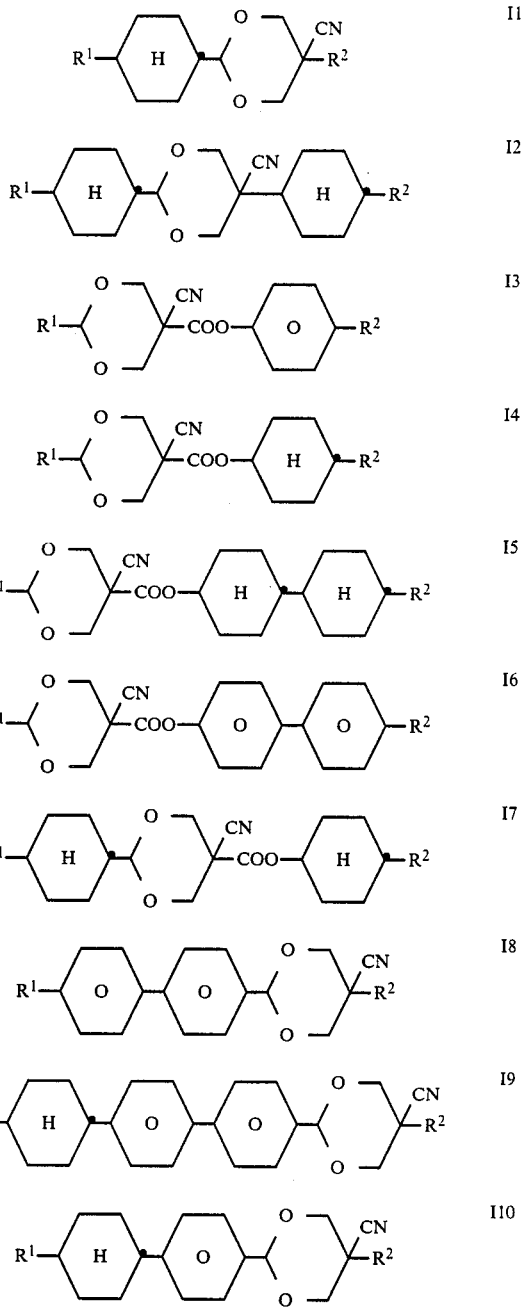

In the compounds of the abovementioned formulae I1 to I10 $R^1$ and $R^2$ preferably are branched or straight-chain alkyl or alkoxy groups each having 2–10 C atoms. 1,4-phenylene groups may be laterally substituted by fluorine. In fozmula I alkyl groups having CH2 replaced by —CH=CH— have from 2–10 C atoms.

In the compounds of the abovementioned formulae, those stereoisomers are preferred in which the substituents $R^1$—, $R^1$—$A^4$— and R —A —Z — or $R^2$—$A^2$—$Z^1$—$A^4$— in the 2- and 5-positions of the ring A are trans relative to one another and assume the equatorial position, while the additional substituent on A in the 2- or 5-position (for example $X^1$ or $X^2$) assumes an axial position. These compounds are as a rule more stable; in many cases, the cis compounds (or mixtures) can be converted into the trans compounds by treatment with a base, for example with K tert.-butylate in an inert solvent such as dimethyl sulfoxide. If the additional substituent on A is in the 4-position, it can assume an equatorial or axial position. Preferably, it is in the equatorial position like the substituents in the 2- and 5-positions.

The compounds of the formula I are prepared by methods known per se, such as are described in the literature (for example in the standard textbooks, such as Houben-Weyl, Methoden der Organischen Chemie [Methods of Organic Chemistry], Georg-Thieme-Verlag, Stuttgart), and in particular under reaction conditions which are known and suitable for the said conversions. Variants which are known per se and are not mentioned here in more detail can also be utilized.

If desired, the starting materials can also be formed in situ, in such a way that they are not isolated from the reaction mixture but immediately converted further to give the compounds of the formula I.

Thus, the compounds of the formula I can be prepared by reacting a corresponding aldehyde or a corresponding ketone with a corresponding diol or dithiol. The preparation of compounds of the formula I, in which $A^1$ is —A—, is discussed in more detail below. Compounds of the formula I, in which $A^1$ is —$A^4$—A— or —A—$A^4$—, can be prepared by analogous processes.

Thus, compounds in which A is a 1,3-dioxane-2,5-diyl or 1,3-dithiane-2,5-diyl group which is substituted in the 2-position by alkyl having 1-10 C atoms, are obtainable by condensing a ketone of the formula (a) with a diol or dithiol of the formula (b) or by condensing a ketone of the formula (c) with a diol or dithiol of the formula (d).

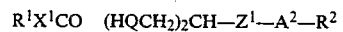

(a)         (b)

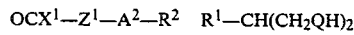

(c)         (d)

In the formulae (a)–(h) above and below, $R^1$, $R^2$, $A^2$ and $Z^1$ have the meanings given above. Q is O or S. $X^1$ is alkyl having 1-10 C atoms, preferably straight-chain alkyl having 1-5 C atoms, and particularly preferably is methyl. $X^2$ is alkyl, alkoxy, fluorinated alkyl or fluorinated alkoxy each having 1-5 C atoms, or is F, Cl, Br or CN. Preferred meanings of $X^3$ are —$CH_3$, —$CH_2CH_3$, —$OCH_3$, —$CF_3$, —$CF_2CF_3$, F, Cl and CN; F and CN are particularly preferred.

Compounds in which A is 1,3-dioxane-2,5-diyl or a 1,3-dithiane-2,5-diyl group substituted in the 5-position by alkyl, alkoxy, fluorinated alkyl or fluorinated alkoxy each having 1-5 C atoms, or by F, Cl, Br or CN, are obtainable by condensing an aldehyde of the formula (e) with a diol or dithiol of the formula (f) or by condensing a ketone of the formula (g) with a diol or dithiol of the formula (h).

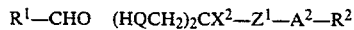

(e)         (f)

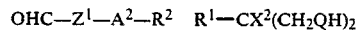

(g)         (h)

Compounds in which A is substituted in the 2- and 5-positions, are obtainable by condensing a ketone of the formula (a) with a diol or dithiol of the formula (f) or by condensing a ketone of the formula (c) with a diol or dithiol of the formula (h).

Compounds in which A is a 1,3-dioxane-2,5-diyl or 1,3-dithiane-2,5-diyl group substituted in the 4-position by alkyl having 1-10 C atoms, are obtainable by condensing a corresponding 2,3-disubstituted 1,3-diol or 1,3-dithiol with a corresponding aldehyde.

The starting materials, in particular (a) to (h), can be employed as such or in the form of their reactive derivatives. Suitable reactive derivatives are above all the acetals.

The condensation of the abovementioned starting materials is preferably carried out in the presence of an inert solvent, such as benzene or toluene, and/or a catalyst, for example a strong acid such as sulfuric acid, benzene- or p-toluene-sulfonic acid, at temperatures between about 20° and about 150°, preferably between 80° and 120°.

Some of the starting materials mentioned and their reactive derivatives are known, and some of them can be prepared without difficulty by standard methods of organic chemistry from compounds known in the literature. For example, the aldehydes are obtainable by oxidizing corresponding alcohols or by reducing corresponding carboxylic acids or derivatives thereof. The ketones are obtainable, for example, by reacting corresponding nitriles (obtainable from the corresponding carboxylic acids) with Grignard compounds. The diols are obtainable, for example, by reducing corresponding diesters which in turn can be prepared by standard methods from malonic esters. The dithiols are obtainable by reacting corresponding dihalides (obtainable from the diols) with NaSH.

Esters of the formula I (in which $Z^1$ and/or $Z^2$ are —CO—O— or —O—CO— and/or $R^1$ and/or $R^2$ are an alkyl group in which one $CH_2$— group is replaced by —O—CO— or —CO—O—) can also be obtained by esterifying corresponding carboxylic acids with alcohols or phenols or reactive derivatives thereof.

Suitable reactive derivatives of the said carboxylic acids are in particular the acid halides, above all the chlorides and bromides, and also the anhydrides, for example also mixed anhydrides, azides or esters, in particular alkyl esters having 1-4 C atoms in the alkyl group.

Possible reactive derivatives of the said alcohols or phenols are in particular the corresponding metal alcoholates or phenolates, preferably those of an alkali metal such as Na or K.

The esterification is advantageously carried out in the presence of an inert solvent. In particular, ethers such as diethyl ether, di-n-butyl ether, THF, dioxane or anisole, ketones such as acetone, butanone or cyclohexanone, amides such as DMF or phosphoric acid hexamethyltriamide, hydrocarbons such as benzene, toluene or xylene, halogenohydrocarbons such as carbon tetrachloride or tetrachloroethylene, and sulfoxides such as dimethyl sulfoxide or sulfolan are very suitable. Solvents immiscible with water can at the same time be used advantageously for azeotropically distilling off the water formed in the esterification. Occasionally, an excess of an organic base, for example pyridine, quinoline or triethylamine, can also be used as the solvent for the esterification. The esterification can also be carried out in the absence of a solvent, for example by simply heating the components in the presence of sodium acetate. The reaction temperature is usually between −50° and 250°, preferably between −20° and +80°. At these temperatures, the esterification reactions are as a rule complete after 15 minutes to 48 hours.

The detailed reaction conditions for the esterification depend largely on the nature of the starting materials used. Thus, a free carboxylic acid is reacted with a free alcohol or phenol, as a rule in the presence of a strong acid, for example a mineral acid such as hydrochloric acid or sulfuric acid. A preferred procedure is the reaction of an acid anhydride or in particular an acid chloride with an alcohol, preferably in a basic medium, important bases being in particular alkali metal hydroxides such as sodium or potassium hydroxide, alkali metal carbonates or hydrogen carbonates such as sodium carbonate, sodium hydrogen carbonate, potassium carbonate or potassium hydrogen carbonate, alkali metal acetates such as sodium or potassium acetate, alkaline earth metal hydroxides such as calcium hydroxide, or organic bases such as triethylamine, pyridine, lutidine, collidine or quinoline. Another preferred method for carrying out the esterification comprises first converting the alcohol or the phenol into the sodium or potassium alcoholate or phenolate, for example by treatment with ethanolic sodium or potassium hydroxide solution, isolating this alcoholate or phenolate and suspending it together with sodium hydrogen carbonate or potassium carbonate in acetone or diethyl ether with stirring and treating this suspension with a solution of the acid chloride or anhydride in diethyl ether, acetone or DMF, preferably at temperatures between −25° and +20°.

For the preparation of nitriles of the formula I (in which $R^1$ and/or $R^2$ and/or $R^3$ are CN and/or A is a 1,3-dioxane-2,5-diyl or 1,3-dithiane-2,5-diyl group substituted by CN in the 5-position), corresponding acid amide, for example those in which a $CONH_2$ group is in the place of the radical CN, can be dehydrated.

The amides are obtainable, for example, from corresponding esters or acid halides by reaction with ammonia. Examples of suitable dehydrating agents are inorganic acid chlorides, such as $SOCl_2$, $PCl_3$, $PCl_5$, $POCl_3$, $SO_2C_2$, $COCl_2$ and also $P_2O_5$, $P_2S_5$ and $AlCl_3$ (for example as a double compound with NaCl), aromatic sulfonic acids and sulfonic acid halides. This reaction can be carried out in the presence or absence of an inert solvent at temperatures between about 0° and 150°; examples of possible solvents are bases such as pyridine or triethylamine, aromatic hydrocarbons such as benzene, toluene or xylene, or amides such as DMF.

For the preparation of the abovementioned nitriles of the formula I, it is also possible to react corresponding acid halides, preferably the chlorides, with sulfamide, preferably in an inert solvent such as tetramethylene sulfone at temperatures between about 80° and 150°, preferably at 120°. After usual working-up, the nitriles can be isolated directly.

The dielectrics according to the invention consist of 2 to 20, preferably 3 to 15, components including at least one compound of the formula I. The other constituents are preferably selected from the nematic or nematogenic substances, in particular the known substances from the classes of the azoxybenzenes, benzylideneanilines, biphenyls, terphenyls, phenyl or cyclohexyl benzoates, phenyl or cyclohexyl cyclohexane-carboxylates, phenylcyclohexanes, cyclohexylbiphenyls, cyclohexylcyclohexanes, cyclohexylnaphthalenes, 1,4-bis-cyclohexylbenzenes, 4,4'-bis-cyclohexylbiphenyls, phenyl- or cyclohexyl-pyrimidines, phenyl- or cyclohexyl-pyridazines and their N-oxides, phenyl- or cyclohexyl-dioxanes, phenyl- or cyclohexyldithianes, cyclohexylethylbenzenes, stilbenes or halogenated stilbenes, benzyl phenyl ethers, tolanes and substituted cinnamic acids.

The most important compounds which can be used as constituents of such liquid-crystalline dielectrics can be characterized by the formula II

$$R'—L—G—E—R'' \qquad \text{II}$$

in which L and E each are a carbocyclic or heterocyclic ring system selected from the group comprising 1,4-disubstituted benzene and cyclohexane rings, 4,4'-disubstituted biphenyl, phenylcyclohexane and cyclohexylcyclohexane systems, 2,5-disubstituted pyrimidine and 1,3-dioxane rings, 2,6-disubstituted naphthalene, di- and tetra-hydronaphthalene, quinazoline and tetrahydroquinazoline, it being possible for the 1,4-disubstituted cyclohexane rings additionally to carry a cyano group in the 1- or 4-position, G is —CH=CH—, —CH=CY—, —C≡C—, —CO—O—, —CO—S—, —CH=N—, —N(O)=N—, —CH=N(O)—, —CH$_2$—CH$_2$—, —CH$_2$—O—, —CH$_2$—S—, —COO—Phe—COO—, or a C—C single bond, Y is halogen, preferably chlorine, or —CN, and R' and R'' are alkyl, alkoxy, alkanoyloxy or alkoxycarbonyloxy having up to 18, preferably up to 8, carbon atoms, or one of these radicals can also be CN, NC, $NO_2$, $CF_3$, F, Cl or Br.

In most of these compounds R' and R'' differ from one another, one of these radicals being an alkyl or alkoxy group in most cases. However, other variants of the envisaged substituents are also widely used. Many such substances or mixtures thereof are commercially available. All these substances can be prepared by methods known from the literature.

The dielectrics according to the invention contain as a rule at least 30, preferably 50–99, in particular 60–98, percent by weight of the compounds of the formula I and II. Of these, preferably at least 5 percent by weight, and in most cases even 10–30 percent by weight, represent one or more compounds of the formula I. However, the invention also comprises those liquid-crystalline dielectrics, to which, for example for doping purposes, only less than 5 percent by weight, for example 0.1 to 3 percent by weight, of one or more compounds of the formula I have been added. On the other hand, the compounds of the formula I can amount to as much as 60 percent by weight of the dielectrics according to the invention. Preferably, the liquid-crystalline dielectrics according to the invention contain 10 to 30 percent by weight of one or more compounds of the formula I.

The dielectrics according to the invention are prepared in the conventional manner. As a rule, the components are dissolved in one another, preferably at an elevated temperature. By means of suitable additives, the liquid-crystalline dielectrics according to the invention can be modified in such a way that they can be used in any hitherto disclosed types of liquid crystal display elements.

Such additives are known to those skilled in the art and are described in great detail in the literature. For example, conductive salts, preferably ethyldimethyl-dodecyl-ammonium 4-hexyloxybenzoate, tetrabutyl-ammonium tetraphenylboranate or complex salts of crown ethers (cf. for example I. Haller et al., Mol. Cryst. Liq. Cryst. Volume P4. pages 249–258 (1973))

can be added for improving the conductivity, dichroic dyes can be added for the preparation of colored guest-/host systems, or substances for varying the dielectric anisotropy, the viscosity and/or the orientation of the nematic phases can be added. Such substances are described, for example, in German Offenlegungsschriften Nos. 2,209,127, 2,240,864, 2,321,632, 2,338,281, 2,450,088, 2,637,430, 2,853,728 and 2,902,177.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the preceding text and the following examples, all temperatures are set forth uncorrected in degrees Celsius and all parts and percentages are by weight, M. —melting point, and C. =clear point; unless otherwise indicated.

"Usual working-up" means: water is added, the mixture is extracted with methylene chloride, the phases are separated, the organic phase is dried and evaporated, and the product is purified by crystallization and/or chromatography.

EXAMPLE 1

6.5 g of 4-cyanobenzaldehyde and 9.5 g of 2-methyl-2-heptyl-1,3-propanediol are dissolved in 150 ml of toluene, a spatula tip of p-toluenesulfonic acid is added and the mixture is heated under a water separator until water of reaction is no longer formed. After cooling, the mixture is washed with sodium bicarbonate solution and with water until neutral and dried over sodium sulfate, and the toluene is distilled off. Isomer-free r-2-(4-cyanophenyl)-trans-5-n-heptyl-cis-5-methyl-1,3-dioxane, M. 64°C., is obtained from the residue via the thiourea inclusion compound.

The following are prepared analogously:

r-2-(4-cyanophenyl)-trans-5-hexyl-cis-5-methyl-1,3-dioxane r-2-(4-cyanophenyl)-trans-5-pentyl-cis-5-methyl-1,3-dioxane r-2-(4-cyanophenyl)-trans-5-butyl-cis-5-methyl-1,3-dioxane r-2-(4-cyanophenyl)-trans-5-propyl-cis-5-methyl-1,3-dioxane r-2-(4-cyanophenyl)-trans-5-ethyl-cis-5-methyl-1,3-dioxane r-2-(4-propylphenyl)-trans-5-ethyl-cis-5-methyl-1,3-dioxane r-2-(4-propylphenyl)-trans-5-propyl-cis-5-methyl-1,3-dioxane r-2-(4-propylphenyl)-trans-6-butyl-cis-5-methyl-1,3-dioxane r-2-(4-propylphenyl)-trans-5-pentyl-cis-5-methyl-1,3-dioxane r-2-(4-propylphenyl)-trans-5-hexyl-cis-5-methyl-1,3-dioxane r-2-(4-propylphenyl)-trans-5-heptyl-cis-5-methyl-1,3-dioxane r-2-(4-pentylphenyl)-trans-5-ethyl-cis-5-methyl-1,3-dioxane r-2-(4-pentylphenyl)-trans-5-propyl-cis-5-methyl-1,3-dioxane r-2-(4-pentylphenyl)-trans-5-butyl-cis-5-methyl-1,3-dioxane r-2-(4-pentylphenyl)-trans-5-pentyl-cis-5-methyl-1,3-dioxane r-2-(4-pentylphenyl)-trans-5-hexyl-cis-5-methyl-1,3-dioxane r-2-(4-pentylphenyl)-trans-5-heptyl-cis-5-methyl-1,3-dioxane

EXAMPLE 2

13.6 g of 4-(trans-4-n-pentylcyclohexyl)-acetophenone and 6 g of 2-n-propyl-1,3-propanediol are heated with a spatula tip of p-toluenesulfonic acid in 200 ml of toluene for 5 hours under a water separator. The mixture is allowed to cool, washed with sodium bicarbonate solution and with water until neutral and dried over sodium sulfate, and the toluene is distilled off. Pure r-2-[4-(trans-4-n-pentylcyclohexyl)-phenyl]-2 -methyl-5-n-propyl-1,3-dioxane is obtained from residue by repeated recrystallization from ethanol.

The following are prepared analogously:

r-2-[4-trans-4-pentylcyclohexyl)-phenyl]-2-methyl-t-5-methyl-1,3-dioxane r-2-[4-trans-4-pentylcyclohexyl)-phenyl]-2-methyl-t-5-ethyl-1,3-dioxane r-2-[4-trans-4-pentylcyclohexyl)-phenyl]-2-methyl-t-5-butyl-1,3-dioxane r-2-[4-trans-4-pentylcyclohexyl)-phenyl]-2-methyl-t-5-pentyl-1,3-dioxane, M. 79° r-2-[4-trans-4-pentylcyclohexyl)-phenyl]-2-methyl-t-5-hexyl-1,3-dioxane r-2-[4-trans-4-pentylcyclohexyl)-phenyl]-2-methyl-t-5-heptyl-1,3-dioxane r-2-[4-(trans-4-propylcyclohexyl)-phenyl]-2-methyl-t-5-methyl-1,3-dioxane r-2-[4-(trans-4-propylcyclohexyl)-phenyl]-2-methyl-t-5-ethyl-1,3-dioxane r-2-[4-(trans-4-propylcyclohexyl)-phenyl]-2-methyl-t-5-propyl-1,3-dioxane r-2-[4-(trans-4-propylcyclohexyl)-phenyl]-2-methyl-t-5-butyl-1,3-dioxane r-2-[4-(trans-4-propylcyclohexyl)-phenyl]-2-methyl-t-5-pentyl-1,3-dioxane r-2-[4-(trans-4-propylcyclohexyl)-phenyl]-2-methyl-t-5-heptyl-1,3-dioxane r-2-[4-(trans-4-propylcyclohexyl)-biphenyl-4'-yl]-2-methyl-t-5-methyl-1,3-dioxane r-2-[4-(trans-4-propylcyclohexyl)-biphenyl-4'-yl]-2-methyl-t-5-ethyl-1,3-dioxane r-2-[4-(trans-4-propylcyclohexyl)-biphenyl-4'-yl]-2-methyl-t-5-propyl-1,3-dioxane r-2-[4-(trans-4-propylcyclohexyl)-biphenyl-4'-yl]-2-methyl-t-5-butyl-1,3-dioxane r-2-[4-(trans-4-propylcyclohexyl)-biphenyl-4'-yl]-2-methyl-t-5-pentyl-1,3-dioxane r-2-[4-(trans-4-propylcyclohexyl)-biphenyl-4'-yl]-2-methyl-t-5-heptyl-1,3-dioxane r-2-[4-(trans-4-pentylcyclohexyl)-biphenyl-4'-yl]-2-methyl-t-5-methyl-1,3-dioxane r-2-[4-(trans-4-pentylcyclohexyl)-biphenyl-4'-yl]-2-methyl-t-5-ethyl, 1,3-dioxane r-2-[4-(trans-4-pentylcyclohexyl)-biphenyl-4'-yl]-2-methyl-t-5-propyl-1,3-dioxane r-2-[4-(trans-4-pentylcyclohexyl)-biphenyl-4'-yl]-2-methyl-t-5-butyl-1,3-dioxane r-2-[4-(trans-4-pentylcyclohexyl)-biphenyl-4'-yl]-2-methyl-t-5-pentyl-1,3-dioxane r-2-[4-(trans-4-pentylcyclohexyl)-biphenyl-4'-yl]-2-methyl-t-5-heptyl-1,3-dioxane

EXAMPLE 3

6.4 g of trans-4-ethylcyclohexanol, 0.6 g of 4-N,N-dimethylaminopyridine and 10.8 g of dicyclohexylcarbodiimide are added successively at 5° with stirring to 14.9 g of 2-(trans-4-n-pentylcyclohexyl)-5-methyl-1,3-dioxane-5-carboxylic acid (obtainable by condensing trans-4-n-pentylcyclohexanecarbaldehyde with dihydroxypivalic acid) dissolved in 250 ml of dichloromethane. The mixture is allowed to come to room temperature and stirring is continued overnight. For working up, the urea which has precipitated is filtered off, the filtrate is concentrated and the residue is recrystallized. This gives trans-4-ethylcyclohexyl r-2-(trans-4-n-pentylcyclohexyl)c-5-methyl-1,3-dioxane-t-5-carboxylate, M. 99°.

The following are prepared analogously: trans-4-propylcyclohexyl r-2-(trans-4-pentylcyclohexyl)-c-5-methyl-1,3-dioxane-5-carboxylate trans-4-butylcyclohexyl r-2-(trans-4-pentylcyclohexyl)-c-5-methyl-1,3-dioxane-5-carboxylate trans-4-pentylcyclohexyl r-2-(trans-4-pentylcyclohexyl)-c-5-methyl-1,3-dioxane-5-carboxylate trans-4-heptylcyclohexyl r-2-(trans-4-pentylcyclohexyl)-c-5-methyl-1,3-dioxane-5-carboxylate trans-4-methylcyclohexyl r-2-(trans-4-propylcyclohexyl)-c-5-methyl-1,3-dioxane-5-carboxylate trans-4-ethylcyclohexyl r-2-(trans-4-propylcyclohexyl)-c-5-methyl-1,3-dioxane-5-carboxylate trans-4-propylcyclohexyl r-2-(trans-4-propylcyclohexyl)-c-5-methyl-1,3-dioxane-5-carboxylate trans-4-butylcyclohexyl r-2-(trans-4-propylcyclohexyl)-c-5-methyl-1,3-dioxane-5-carboxylate trans-4-pentylcyclohexyl r-2-(trans-4-propylcyclohexyl)-c-5-methyl-1,3-dioxane-5-carboxylate trans-4-heptylcyclohexyl r-2-(trans-4-propylcyclohexyl)-c-5-methyl-1,3-dioxane-5-carboxylate p-methylphenyl r-2-(trans-4-propylcyclohexyl)-c-5-methyl-1,3-dioxane-5-carboxylate p-ethylphenyl r-2-(trans-4-propylcyclohexyl)-c-5-methyl-1,3-dioxane-5-carboxylate p-propylphenyl r-2-(trans-4-propylcyclohexyl)-c-5-methyl-1,3-dioxane-5-carboxylate p-butylphenyl r-2-(trans-4-propylcyclohexyl)-c-5-methyl-1,3-dioxane-5-carboxylate p-pentylphenyl r-2-(trans-4-propylcyclohexyl)-c-5-methyl-1,3-dioxane-5-carboxylate p-ethoxyphenyl r-2-(trans-4-propylcyclohexyl)-c-5-methyl-1,3-dioxane-5-carboxylate p-butoxyphenyl r-2-(trans-4-propylcyclohexyl)-c-5-methyl-1,3-dioxane-5-carboxylate p-cyanophenyl r-2-(trans-4-propylcyclohexyl)-c-5-methyl-1,3-dioxane-5-carboxylate p-methylphenyl r-2-(p-propylphenyl)-c-5-methyl-1,3-dioxane-5-carboxylate p-ethylphenyl r-2-(p-propylphenyl)-c-5-methyl-1,3-dioxane-5-carboxylate p-propylphenyl r-2-(p-propylphenyl)-c-5-methyl-1,3-dioxane-5-carboxylate p-butylphenyl r-2-(p-propylphenyl)-c-5-methyl-1,3-dioxane-5-carboxylate p-pentylphenyl r-2-(p-propylphenyl)-c-5-methyl-1,3-dioxane-5-carboxylate p-ethoxyphenyl r-2-(p-propylphenyl)-c-5-methyl-1,3-dioxane-5-carboxylate p-butoxyphenyl r-2-(p-propylphenyl)-c-5-methyl-1,3-dioxane-5-carboxylate p-cyanophenyl r-2-(p-propylphenyl)-c-5-methyl-1,3-dioxane-5-carboxylate

EXAMPLE 4 trans,trans-4-n-Propylcyclohexyl-4'-carbaldehyde is condensed with α,α-bishydroxymethylcaproic acid, and the acid obtained is converted into the acid chloride by heating with thionylchloride and then by treatment with ammonia into the amide. 7.9 g of the amide are heated for 15 hours to 80° with 36 g of thionyl chloride and 0.2 g of dimethylformamide in 200 ml of toluene.

The excess thionyl chloride and half the toluene are then distilled off. The remaining solution is washed with sodium bicarbonate and with water until neutral and dried over sodium sulfate. After the solvent has been evaporated, repeated recrystallization gives pure trans, trans-4-n-propyl-4'-(trans-5-n-butyl-cis-5-cyano-1,3-dioxan-2-yl)-bicyclohexyl.

The following are prepared analogously:

trans,trans-4-propyl-4'-(trans-5-methyl-cis-5-cyano-1,3-dioxan-2-yl)-bicyclohexyl trans,trans-4-propyl-4'-(trans-5-ethyl-cis-5-cyano-1,3-dioxan-2-yl)-bicyclohexyl trans,trans-4-propyl-4'-(trans-5-propyl-cis-5-cyano-1,3-dioxan-2-yl)-bicyclohexyl trans,trans-4-propyl-4'-(trans-5-butyl-cis-5-cyano-1,3-dioxan-2-yl)-bicyclohexyl trans,trans-4-propyl-4'-(trans-5-pentyl-cis-5-cyano-1,3-dioxan-2-yl)-bicyclohexyl trans,trans-4-propyl-4'-(trans-5-heptyl-cis-5-cyano-1,3-dioxan-2-yl)-bicyclohexyl trans,trans-4-pentyl-4'-(trans-5-methyl-cis-5-cyano-1,3-dioxan-2-yl)-bicyclohexyl trans,trans-4-pentyl-4'-(trans-5-ethyl-cis-5-cyano-1,3-dioxan-2-yl)-bicyclohexyl trans,trans-4-pentyl-4'-(trans-5-propyl-cis-5-cyano-1,3-dioxan-2-yl)-bicyclohexyl trans,trans-4-pentyl-4'-(trans-5-butyl-cis-5-cyano-1,3-dioxan-2-yl)-bicyclohexyl trans,trans-4-pentyl-4'-(trans-5-pentyl-cis-5-cyano-1,3-dioxan-2-yl)-bicyclohexyl trans,trans-4-pentyl-4'-(trans-5-heptyl-cis-5-cyano-1,3-dioxan-2-yl)-bicyclohexyl trans-4-propyl-(trans-5-methyl-cis-5-cyano-1,3-dioxan-2-yl)-cyclohexane trans-4-propyl-(trans-5-ethyl-cis-5-cyano-1,3-dioxan-2-yl)-cyclohexane trans-4-propyl-(trans-5-propyl-cis-5-cyano-1,3-dioxan-2-yl)-cyclohexane trans-4-propyl-(trans-5-butyl-cis-5-cyano-1,3-dioxan-2-yl)-cyclohexane trans-4-propyl-(trans-5-pentyl-cis-5-cyano-1,3-dioxan-2-yl)-cyclohexane trans-4-propyl-(trans-5-heptyl-cis-5-cyano-1,3-dioxan-2-yl)-cyclohexane trans-4-pentyl-(trans-5-methyl-cis-5-cyano-1,3-dioxan-2-yl)-cyclohexane trans-4-pentyl-(trans-5-ethyl-cis-5-cyano-1,3-dioxan-2-yl)-cyclohexane trans-4-pentyl-(trans-5-propyl-cis-5-cyano-1,3-dioxan-2-yl)-cyclohexane trans-4-pentyl-(trans-5-butyl-cis-5-cyano-1,3-dioxan-2-yl)-cyclohexane trans-4-pentyl-(trans-5-pentyl-cis-5-cyano-1,3-dioxan-2-yl)-cyclohexane trans-4-pentyl-(trans-5-heptyl-cis-5-cyano-1,3-dioxan-2-yl)-cyclohexane trans-4-butyl-(trans-5-methyl-cis-5-cyano-1,3-dioxan-2-yl)-cyclohexane
trans-4-butyl-(trans-5-ethyl-cis-5-cyano-1,3-dioxan-2-yl)-cyclohexane
trans-4-butyl-(trans-5-propyl-cis-5-cyano-1,3-dioxan-2-yl)-cyclohexane
trans-4-butyl-(trans-5-butyl-cis-5-cyano-1,3-dioxan-2-yl)-cyclohexane
trans-4-butyl-(trans-pentyl-cis-5-cyano-1,3-dioxan-2-yl)-cyclohexane
trans-4-butyl-(trans-5-heptyl-cis-5-cyano-1,3-dioxan-2-yl)-cyclohexane

EXAMPLE 5

2-(trans-4-n-Hexylcyclohexyl)-5-n-hexyl-1,3-dithiane (East German Patent Specification No. 158,480) is reacted in THF at room temperature with an equimolar quantity of butyllithium. An equimolar quantity of methyl iodide is added to the solution of the carbanion obtained and the mixture is stirred overnight. Usual working-up gives r-2-(trans-4-n-hexylcyclohexyl)-trans-5-n-hexyl-cis-5-methyl-1,3-dithiane.

The following are prepared analogously:
r-2-(trans-4-hexylcyclohexyl)-trans-5-ethyl-cis-5-methyl-1,3-dithiane
r-2-(trans-4-hexylcyclohexyl)-trans-5-propyl-cis-5-methyl-1,3-dithiane
r-2-(trans-4-hexylcyclohexyl)-trans-5-butyl-cis-5-methyl-1,3-dithiane
r-2-(trans-4-hexylcyclohexyl)-trans-5-pentyl-cis-5-methyl-1,3-dithiane
r-2-(trans-4-hexylcyclohexyl)-trans-5-heptyl-cis-5-methyl-1,3-dithiane
r-2-(trans-4-pentylcyclohexyl)-trans-5-ethyl-cis-5-methyl-1,3-dithiane
r-2-(trans-4-pentylcyclohexyl)-trans-5-propyl-cis-5-methyl-1,3-dithiane
r-2-(trans-4-pentylcyclohexyl)-trans-5-butyl-cis-5-methyl-1,3-dithiane
r-2-(trans-4-pentylcyclohexyl)-trans-5-pentyl-cis-5-methyl-1,3-dithiane
r-2-(trans-4-pentylcyclohexyl)-trans-5-heptyl-cis-5-methyl-1,3-dithiane
r-2-(trans-4-propylcyclohexyl)-trans-5-ethyl-cis-5-methyl-1,3-dithiane
r-2-(trans-4-propylcyclohexyl)-trans-5-propyl-cis-5-methyl-1,3-dithiane
r-2-(trans-4-propylcyclohexyl)-trans-5-butyl-cis-5-methyl-1,3-dithiane
r-2-(trans-4-propylcyclohexyl)-trans-5-pentyl-cis-5-methyl-1,3-dithiane
r-2-(trans-4-propylcyclohexyl)-trans-5-heptyl-cis-5-methyl-1,3-dithiane

EXAMPLE 6

A mixture of 0.1 mol of p-cyanobenzaldehyde, 0.1 mol of 3-hydroxymethyl-2-octanol, 200 ml of benzene and 150 mg of p-toluenesulfonic acid is boiled under a water separator until the reaction is complete. Usual working-up gives 2-p-cyanophenyl-5-n-pentyl-4-methyl-1,3-dioxane.

The following are prepared analogously:
2-p-cyanophenyl-5-methyl-4-methyl-1,3-dioxane
2-p-cyanophenyl-5-ethyl-4-methyl-1,3-dioxane
2-p-cyanophenyl-5-propyl-4-methyl-1,3-dioxane
2-p-cyanophenyl-5-butyl-4-methyl-1,3-dioxane
2-p-cyanophenyl-5-hexyl-4-methyl-1,3-dioxane
2-p-cyanophenyl-5-heptyl-4-methyl-1,3-dioxane
2-p-propylphenyl-5-methyl-4-methyl-1,3-dioxane
2-p-propylphenyl-5-ethyl-4-methyl-1,3-dioxane
2-p-propylphenyl-5-propyl-4-methyl-1,3-dioxane
2-p-propylphenyl-5-butyl-4-methyl-1,3-dioxane
2-p-propylphenyl-5-pentyl-4-methyl-1,3-dioxane
2-p-propylphenyl-5-heptyl-4-methyl-1,3-dioxane
2-p-pentylphenyl-5-methyl-4-methyl-1,3-dioxane
2-p-pentylphenyl-5-ethyl-4-methyl-1,3-dioxane
2-p-pentylphenyl-5-propyl-4-methyl-1,3-dioxane
2-p-pentylphenyl-5-butyl-4-methyl-1,3-dioxane
2-p-pentylphenyl-5-pentyl-4-methyl-1,3-dioxane
2-p-pentylphenyl-5-heptyl-4-methyl-1,3-dioxane
2-p-ethoxyphenyl-5-methyl-4-ethyl-1,3-dioxane
2-p-ethoxyphenyl-5-ethyl-4-methyl-1,3-dioxane
2-p-ethoxyphenyl-5-propyl-4-methyl-1,3-dioxane
2-p-ethoxyphenyl-5-butyl-4-methyl-1,3-dioxane
2-p-ethoxyphenyl-5-pentyl-4-methyl-1,3-dioxane
2-p-ethoxyphenyl-5-heptyl-4-methyl-1,3-dioxane
2-p-butoxyphenyl-5-methyl-4-methyl-1,3-dioxane
2-p-butoxyphenyl-5-ethyl-4-methyl-1,3-dioxane
2-p-butoxyphenyl-5-propyl-4-methyl-1,3-dioxane
2-p-butoxyphenyl-5-butyl-4-methyl-1,3-dioxane
2-p-butoxyphenyl-5-pentyl-4-methyl-1,3-dioxane
2-p-butoxyphenyl-5-heptyl-4-methyl-1,3-dioxane

EXAMPLE 7

The acid chloride, obtained from 24 g of 2-p-cyanophenyl-5-n-hexyl-4-methyl-1,3-dioxane (Example 6) by hydrolysis and treatment with $SOCl_2$, is dissolved in 150 ml of toluene, 10 ml of pyridine and an equimolar quantity of p-cyanophenol are added and the mixture is boiled for 2 hours. After cooling and usual working-up, this gives p-cyanophenyl p-(4-methyl-5-n-hexyl-1,3-dioxan-2-yl)-benzoate, M. 98°, C. 126°.

The following are prepared analogously:
p-cyanophenyl p-(4-methyl-5-ethyl-1,3-dioxan-2-yl)-benzoate
p-cyanophenyl p-(4-methyl-5-propyl-1,3-dioxan-2-yl)-benzoate
p-cyanophenyl p-(4-methyl-5-butyl-1,3-dioxan-2-yl)-benzoate
p-cyanophenyl p-(4-methyl-5-pentyl-1,3-dioxan-2-yl)-benzoate
p-cyanophenyl p-(4-methyl-5-heptyl1,3-dioxan-2-yl)-benzoate
p-ethoxyphenyl p-(4-methyl-5-ethyl-1,3-dioxan-2-yl)-benzoate
p-ethoxyphenyl p-(4-methyl-5-propyl-1,3-dioxan-2-yl)-benzoate
p-ethoxyphenyl p-(4-methyl-5-butyl-1,3-dioxan-2-yl)-benzoate
p-ethoxyphenyl p-(4-methyl-5-pentyl-1,3-dioxan-2-yl)-benzoate
p-ethoxyphenyl p-(4-methyl-5-heptyl-1,3-dioxan-2-yl)-benzoate
p-propylphenyl p-(4-methyl-5-ethyl-1,3-dioxan-2-yl)-benzoate
p-propylphenyl p-(4-methyl-5-propyl-1,3-dioxan-2-yl)-benzoate
p-propylphenyl p-(4-methyl-5-butyl-1,3-dioxan-2-yl)-benzoate
p-propylphenyl p-(4-methyl-5-pentyl-1,3-dioxan-2-yl)-benzoate
p-propylphenyl p-(4-methyl-5-heptyl-1,3-dioxan-2-yl)-benzoate
trans-4-propylcyclohexyl trans-4-(4-methyl-5-ethyl-1,3-dioxan-2-yl)-cyclohexanecarboxylate trans-4-propylcyclohexyl trans-4-(4-methyl-5-propyl-1,3-dioxan-2-yl)-cyclohexanecarboxylate trans-4-propylcyclohexyl trans-4-(4-methyl-5-butyl-1,3-dioxan-2-yl)-cyclohexanecarboxylate trans-4-propylcyclohexyl trans-4-(4-methyl-5-pentyl-1,3-dioxan-2-yl)-cyclohexanecarboxylate trans-4-propylcyclohexyl trans-4-(4-methyl-5-heptyl-1,3-dioxan-2-yl)-cyclohexanecarboxylate

EXAMPLE 8

A mixture of 2.8 g of trans,trans-4-n-pentylbicyclohex-4'-yl methyl ketone [obtainable from trans,trans-4-pentylcyclohexylcyclohexane-4'-carbonitrile and methyl magnesium bromide], 1.5 g of 2-n-pentyl-1,3-propanediol, 200 ml of toluene and 20 mg of p-toluenesulfonic acid is heated for 5 hours under a water separator. The mixture is allowed to cool and is worked up as usual. This gives r-2-methyl-c-5-n-pentyl-2-(trans,trans-4-n-pentyl-bicyclohex-4'-yl)-1,3-dioxane.

The following are prepared analogously:

r-2-methyl-c-5-pentyl-2-(trans,trans-4-methylbicyclohex-4'-yl)-1,3-dioxane r-2-methyl-c-5-pentyl-2-(trans,trans-4-ethylbicyclohex-4'-yl)-1,3-dioxane r-2-methyl-c-5-pentyl-2-(trans,trans-4-propylbicyclohex-4'-yl)-1,3-dioxane r-2-methyl-c-5-pentyl-2-(trans,trans,4-butylbicyclohex-4'-yl)-1,3-dioxane r-2-methyl-c-5-pentyl-2-(trans,trans-4-heptylbicyclohex-4'-yl)-1,3-dioxane r-2-methyl-c-5-butyl-2-(trans,trans-4-methylbicyclohex-4'-yl)-1,3-dioxane r-2-methyl-c-5-butyl-2-(trans,trans-4-ethylbicyclohex-4'-yl)-1,3-dioxane r-2-methyl-c-5-butyl-2-(trans,trans-4-propylcyclohex-4'-yl)-1,3-dioxane r-2-methyl-c-5-butyl-2-(trans,trans-4-butylbicyclohex-4'-yl)-1,3-dioxane r-2-methyl-c-5-butyl-2-(trans,trans-4-pentylbicyclohex-4'-yl)-1,3-dioxane r-2-methyl-c-5-butyl-2-(trans,trans-4-heptylbicyclohex-4'-yl)-1,3-dioxane r-2-methyl-c-5-propyl-2-(trans,trans-4-methylbicyclohex-4'-yl)-1,3-dioxane r-2-methyl-c-5-propyl-2-(trans,trans-4-ethylbicyclohex-4'-yl)-1,3-dioxane r-2-methyl-c-5-propyl-2-(trans,trans-4-propylbicyclohex-4'-yl)-1,3-dioxane r-2-methyl-c-5-propyl-2-(trans,trans-4-butylcyclohex-4'-yl)-1,3-dioxane r-2-methyl-c-5-propyl-2-(trans,trans-4-pentylbicyclohex-4'-yl)-1,3-dioxane r-2-methyl-c-5-propyl-2-(trans,trans-4-heptylbicyclohex-4'-yl)-1,3-dioxane r-2-methyl-c-5-ethyl-2-(trans,trans-4-methylbicyclohex-4'-yl)-1,3-dioxane r-2-methyl-c-5-ethyl-2-(trans,trans-4-ethylbicyclohex-4'-yl)-1,3-dioxane r-2-methyl-c-5-ethyl-2-(trans,trans-4-propylbicyclohex-4'-yl)-1,3-dioxane r-2-methyl-c-5-ethyl-2-(trans,trans-4-butylbicyclohex-4'-yl)-1,3-dioxane r-2-methyl-c-5-ethyl-2-(trans,trans-4-pentylbicyclohex-4'-yl)-1,3-dioxane r-2-methyl-c-5-ethyl-2-(trans,trans-4-heptylbicyclohex-4'-yl)-1,3-dioxane

EXAMPLE 9

A mixture of 2.1 g of 2-methyl-2-(trans-4-n-propylcyclohexyl)-1,3-propanediol [obtainable by reacting 4-n-propylcyclohexanone with diethyl malonate, subsequent hydrogenation with NaBH$_4$, alkylation with sodium alcoholate/methyl iodide and reduction of the diester to the diol], 1.0 g of n-hexanal, 150 ml of toluene and 15 mg of p-toluenesulfonic acid is heated for 5 hours under a water separator and, after cooling, worked up as usual. This gives r-5-methyl-c-2-n-pentyl-5-(trans-4-n-propylcyclohexyl)-1,3-dioxane.

The following are prepared analogously:

r-5-methyl-c-2-pentyl-5-(trans-4-methylcyclohexyl)-1,3-dioxane r-5-methyl-c-2-pentyl-5-(trans-4-ethylcyclohexyl)-1,3-dioxane r-5-methyl-c-2-pentyl-5-(trans-4-butylcyclohexyl)-1,3-dioxane r-5-methyl-c-2-pentyl-5-(trans-4-pentylcyclohexyl)-1,3-dioxane r-5-methyl-c-2-pentyl-5-(trans-4-heptylcyclohexyl)-1,3-dioxane r-5-methyl-c-2-butyl-5-(trans-4-methylcyclohexyl)-1,3-dioxane r-5-methyl-c-2-butyl-5-(trans-4-ethylcyclohexyl)-1,3-dioxane r-5-methyl-c-2-butyl-5-(trans-4-propylcyclohexyl)-1,3-dioxane r-5-methyl-c-2-butyl-5-(trans-4-butylcyclohexyl)-1,3-dioxane r-5-methyl-c-2-butyl-5-(trans-4-pentylcyclohexyl)-1,3-dioxane r-5-methyl-c-2-butyl-5-(trans-4-heptylcyclohexyl)-1,3-dioxane r-5-methyl-c-2-propyl-5-(trans-4-methylcyclohexyl)-1,3-dioxane r-5-methyl-c-2-propyl-5-(trans-4-ethylcyclohexyl)-1,3-dioxane r-5-methyl-c-2-propyl-5-(trans-4-propylcyclohexyl)-1,3-dioxane r-5-methyl-c-2-propyl-5-(trans-4-butylcyclohexyl)-1,3-dioxane r-5-methyl-c-2-propyl-5-(trans-4-pentylcyclohexyl)-1,3-dioxane r-5-methyl-c-2-propyl-5-(trans-4-heptylcyclohexyl)-1,3-dioxane r-5-methyl-c-2-ethyl-5-(trans-4-methylcyclohexyl)-1,3-dioxane r-5-methyl-c-2-ethyl-5-(trans-4-ethylcyclohexyl)-1,3-dioxane r-5-methyl-c-2-ethyl-5-(trans-4-propylcyclohexyl)-1,3-dioxane r-5-methyl-c-2-ethyl-5-(trans-4-butylcyclohexyl)-1,3-dioxane r-5-methyl-c-2-ethyl-5-(trans-4-pentylcyclohexyl)-1,3-dioxane r-5-methyl-c-2-ethyl-5-(trans-4-heptylcyclohexyl)-1,3-dioxane r-5-methyl-c-2-ethyl-5-(trans-4-ethoxycyclohexyl)-1,3-dioxane r-5-methyl-c-2-propyl-5-(trans-4-ethoxycyclohexyl)-1,3-dioxane r-5-methyl-c-2-butyl-5-(trans-4-ethoxycyclohexyl)-1,3-dioxane r-5-methyl-c-2-pentyl-5-(trans-4-ethoxycyclohexyl)-1,3-dioxane r-5-methyl-c-2-heptyl-5-(trans-4-ethoxycyclohexyl)-1,3-dioxane r-5-methyl-c-2-ethyl-5-(trans-4-butyryloxycyclohexyl)-1,3-dioxane r-5-methyl-c-2-propyl-5-(trans-4-butyryloxycyclohexyl)-1,3-dioxane r-5-methyl-c-2-butyl-5-(trans-4-butyryloxycyclohexyl)-I5 1,3-dioxane r-5-methyl-c-2-pentyl-5-(trans-4-butyryloxycyclohexyl)-1,3-dioxane r-5-methyl-c-2-heptyl-5-(trans-4-butyryloxycyclohexyl)-1,3-dioxane

EXAMPLE 10

A mixture of 1.9 g of 2-(p-n-propylphenyl)-1,3-propanediol [obtainable by reacting p-n-propylphenylacetonitrile with diethyl oxalate in the presence of alkali, hydrolysis of the nitrile, esterification, decarbonylation and reduction to the diol], 1.0 g of n-butyl methyl ketone, 150 ml of toluene and 15 mg of p-toluenesulfonic acid is heated under a water separator for 5 hours and, after cooling, worked up as usual. This gives r-2-n-butyl-2-methyl-t-5-(p-n-propylphenyl)-1,3-dioxane.

The following are prepared analogously:
r-2-ethyl-2-methyl-t-5-(p-propylphenyl)-1,3-dioxane
r-2-propyl-2-methyl-t-5-(p-propylphenyl)-1,3-dioxane
r-2-pentyl-2-methyl-t-5-(p-propylphenyl)-1,3-dioxane
r-2-hexyl-2-methyl-t-5-(p-propylphenyl)-1,3-dioxane
r-2-heptyl-2-methyl-t-5-(p-propylphenyl)-1,3-dioxane
r-2-ethyl-2-methyl-t-5-(p-butylphenyl)-1,3-dioxane
r-2-propyl-2-methyl-t-5-(p-butylphenyl)-1,3-dioxane
r-2-butyl-2-methyl-t-5-(p-butylphenyl)-1,3-dioxane
r-2-pentyl-2-methyl-t-5-(p-butylphenyl)-1,3-dioxane
r-2-hexyl-2-methyl-t-5-(p-butylphenyl)-1,3-dioxane
r-2-heptyl-2-methyl-t-5-(p-butylphenyl)-1,3-dioxane
r-2-ethyl-2-methyl-t-5-(p-pentylphenyl)-1,3-dioxane
r-2-propyl-2-methyl-t-5-(p-pentylphenyl)-1,3-dioxane
r-2-butyl-2-methyl-t-5-(p-pentylphenyl)-1,3-dioxane
r-2-pentyl-2-methyl-t-5-(p-pentylphenyl)-1,3-dioxane
r-2-hexyl-2-methyl-t-5-(p-pentylphenyl)-1,3-dioxane
r-2-heptyl-2-methyl-t-5-(p-pentylphenyl)-1,3-dioxane
r-2-ethyl-2-methyl-t-5-(p-ethoxyphenyl)-1,3-dioxane
r-2-propyl-2-methyl-t-5-(p-ethoxyphenyl)-1,3-dioxane
r-2-butyl-2-methyl-t-5-(p-ethoxyphenyl)-1,3-dioxane
r-2-pentyl-2-methyl-t-5-(p-ethoxyphenyl)-1,3-dioxane
r-2-hexyl-2-methyl-t-5-(p-ethoxyphenyl)-1,3-dioxane
r-2-heptyl-2-methyl-t-5-(p-ethoxyphenyl)-1,3-dioxane
r-2-ethyl-2-methyl-t-5-(p-butoxyphenyl)-1,3-dioxane
r-2-propyl-2-methyl-t-5-(p-butoxyphenyl)-1,3-dioxane
r-2-butyl-2-methyl-t-5-(p-butoxyphenyl)-1,3-dioxane
r-2-pentyl-2-methyl-t-5-(p-butoxyphenyl)-1,3-dioxane
r-2-hexyl-2-methyl-t-5-(p-butoxyphenyl)-1,3-dioxane
r-2-heptyl-2-methyl-t-5-(p-butoxyphenyl)-1,3-dioxane
r-2-ethyl-2-methyl-t-5-(p-cyanophenyl)-1,3-dioxane
r-2-propyl-2-methyl-t-5-(p-cyanophenyl)-1,3-dioxane
r-2-butyl-2-methyl-t-5-(p-cyanophenyl)-1,3-dioxane
r-2-pentyl-2-methyl-t-5-(p-cyanophenyl)-1,3-dioxane
r-2-hexyl-2-methyl-t-5-(p-cyanophenyl)-1,3-dioxane
r-2-heptyl-2-methyl-t-5-(p-cyanophenyl)-1,3-dioxane

EXAMPLE 11

24.8 g of 2-n-pentyl-5-cyano-1,3-dioxane-5-carboxylic acid chloride [obtainable by reacting cyanoacetate with formaldehyde in the presence of sodium hydrogen carbonate, subsequent acid-catalyzed condensation with hexanal, saponification of the resulting ethyl 2-n-pentyl-5-cyano-1,3-dioxane-5-carboxylate with 10% aqueous-alcoholic KOH and conversion of the free acid by means of cyanuric chloride/triethylamine into the acid chloride] are dissolved in 150 ml of toluene, 8 ml of pyridine and 14 g of trans-4-n-propyl-cyclohexanol are added and the mixture is boiled for 2 hours. After cooling, usual working-up and isomer separation via the thiourea inclusion compound, this gives trans-4-n-propylcyclohexyl 2-n-pentyl-cis-5-cyano-1,3-dioxane-trans-5-carboxylate.

The following are prepared analogously:
trans-4-ethylcyclohexyl 2-pentyl-cis-5-cyano-1,3-dioxane-trans-5-carboxylate
trans-4-butylcyclohexyl 2-pentyl-cis-5-cyano-1,3-dioxane-trans-5-carboxylate
trans-4-pentylcyclohexyl 2-pentyl-cis-5-cyano-1,3-dioxane-trans-5-carboxylate
trans-4-heptylcyclohexyl 2-pentyl-cis-5-cyano-1,3-dioxane-trans-5-carboxylate
trans-4-ethylcyclohexyl 2-butyl-cis-5-cyano-1,3-dioxane-trans-5-carboxylate
trans-4-propylcyclohexyl 2-butyl-cis-5-cyano-1,3-dioxane-trans-5-carboxylate
trans-4-butylcyclohexyl 2-butyl-cis-5-cyano-1,3-dioxane-trans-5-carboxylate
trans-4-pentylcyclohexyl 2-butyl-cis-5-cyano-1,3-dioxane-trans-5-carboxylate
trans-4-heptylcyclohexyl 2-butyl-cis-5-cyano-1,3-dioxane-trans-5-carboxylate
trans-4-ethylcyclohexyl 2-propyl-cis-5-cyano-1,3-dioxane-trans-5-carboxylate
trans-4-propylcyclohexyl 2-propyl-cis-5-cyano-1,3-dioxane-trans-5-carboxylate
trans-4-butylcyclohexyl 2-propyl-cis-5-cyano-1,3-dioxane-trans-5-carboxylate
trans-4-pentylcyclohexyl 2-propyl-cis-5-cyano-1,3-dioxane-trans-5-carboxylate
trans-4-heptylcyclohexyl 2-propyl-cis-5-cyano-1,3-dioxane-trans-5-carboxylate
p-methylphenyl 2-propyl-cis-5-cyano-1,3-dioxane-trans-5-carboxylate
p-ethylphenyl 2-propyl-cis-5-cyano-1,3-dioxane-trans-5-carboxylate
p-propylphenyl 2-propyl-cis-5-cyano-1,3-dioxane-trans-5-carboxylate
p-butylphenyl 2-propyl-cis-5-cyano-1,3-dioxane-trans-5-carboxylate
p-pentylphenyl 2-propyl-cis-5-cyano-1,3-dioxane-trans-5-carboxylate
p-heptylphenyl 2-propyl-cis-5-cyano-1,3-dioxane-trans-5-carboxylate
p-methoxyphenyl 2-propyl-cis-5-cyano-1,3-dioxane-trans-5-carboxylate
p-ethoxyphenyl 2-propyl-cis-5-cyano-1,3-dioxane-trans-5-carboxylate
p-propoxyphenyl 2-propyl-cis-5-cyano-1,3-dioxane-trans-5-carboxylate
p-butoxyphenyl 2-propyl-cis-5-cyano-1,3-dioxane-trans-5-carboxylate
p-cyanophenyl 2-propyl-cis-5-cyano-1,3-dioxane-trans-5-carboxylate
p-methylphenyl 2-butyl-cis-5-cyano-1,3-dioxane-trans-5-carboxylate
p-ethylphenyl 2-butyl-cis-5-cyano-1,3-dioxane-trans-5-carboxylate
p-propylphenyl 2-butyl-cis-5-cyano-1,3-dioxane-trans-5-carboxylate
p-butylphenyl 2-butyl-cis-5-cyano-1,3-dioxane-trans-5-carboxylate p-pentylphenyl 2-butyl-cis-5-cyano-1,3-dioxane-trans-5-carboxylate p-heptylphenyl 2-butyl-cis-5-cyano-1,3-dioxane-trans-5-carboxylate p-methoxyphenyl 2-butyl-cis-5-cyano-1,3-dioxane-trans-5-carboxylate p-ethoxyphenyl 2-butyl-cis-5-cyano-1,3-dioxane-trans-5-carboxylate p-propoxyphenyl 2-butyl-cis-5-cyano-1,3-dioxane-trans-5-carboxylate p-butoxyphenyl 2-butyl-cis-5-cyano-1,3-dioxane-trans-5-carboxylate p-cyanophenyl 2-butyl-cis-5-cyano-1,3-dioxane-trans-5-carboxylate p-methylphenyl 2-pentyl-cis-5-cyano-1,3-dioxane-trans-5-carboxylate p-ethylphenyl 2-pentyl-cis-5-cyano-1,3-dioxane-trans-5-carboxylate p-propylphenyl 2-pentyl-cis-5-cyano-1,3-dioxane-trans-5-carboxylate p-butylphenyl 2-pentyl-cis-5-cyano-1,3-dioxane-trans-5-carboxylate p-pentylphenyl 2-pentyl-cis-5-cyano-1,3-dioxane-trans-5-carboxylate p-heptylphenyl 2-pentyl-cis-5-cyano-1,3-dioxane-trans-5-carboxylate p-methoxyphenyl 2-pentyl-cis-5-cyano-1,3-dioxane-trans-5-carboxylate p-ethoxyphenyl 2-pentyl-cis-5-cyano-1,3-dioxane-trans-5-carboxylate p-propoxyphenyl 2-pentyl-cis-5-cyano-1,3-dioxane-trans-5-carboxylate p-butoxyphenyl 2-pentyl-cis-5-cyano-1,3-dioxane-trans-5-carboxylate p-cyanophenyl 2-pentyl-cis-5-cyano-1,3-dioxane-trans-5-carboxylate trans,trans-4'-methylbicyclohex-4'yl 2-propyl-cis-5-cyano-1,3-dioxane-trans-5-carboxylate trans,trans-4'-ethylbicyclohex-4'-yl 2-propyl-cis-5-cyano-1,3-dioxane-trans-5-carboxylate trans,trans-4'-propylbicyclohex-4-yl 2-propyl-cis-5-cyano-1,3-dioxane-trans-5-carboxylate trans,trans-4'-butylbicyclohex-4-yl 2-propyl-cis-5-cyano-1,3-dioxane-trans-5-carboxylate trans,trans-4'-pentylbicyclohex-4-yl 2-propyl-cis-5-cyano-1,3-dioxane-trans-5-carboxylate trans,trans-4'-heptylbicyclohex-4-yl 2-propyl-cis-5-cyano-1,3-dioxane-trans-5-carboxylate trans,trans-4'-methylbicyclohex-4-yl 2-pentyl-cis-5-cyano-1,3-dioxane-trans-5-carboxylate trans,trans-4'-ethylbicyclohex-4-yl 2-pentyl-cis-5-cyano-1,3-dioxane-trans-5-carboxylate trans,trans-4'-propylbicyclohex-4-yl 2-pentyl-cis-5-cyano-1,3-dioxane-trans-5-carboxylate trans,trans-4'-butylbicyclohex-4-yl 2-pentyl-cis-5-cyano-1,3-dioxane-trans-5-carboxylate trans,trans-4'-pentylbicyclohex-4-yl 2-pentyl-cis-5-cyano-1,3-dioxane-trans-5-carboxylate trans,trans-4'-heptylbicyclohex-4-yl 2-pentyl-cis-5-cyano-1,3-dioxane-trans-5-carboxylate trans-4-methylcyclohexyl 2-(trans-4-propyolcyclohexyl)-cis-5-cyano-1,3-dioxane-trans-5-carboxylate trans-4-ethylcyclohexyl 2-(trans-4-propylcyclohexyl)-cis-5-cyano-1,3-dioxane-trans-5-carboxylate trans-4-propylcyclohexyl 2-(trans-4-propylcyclohexyl)-cis-5-cyano-1,3-dioxane-trans-5-carboxylate trans-4-butylcyclohexyl 2-(trans-4-propylcyclohexyl)-cis-5-cyano-1,3-dioxane-trans-5-carboxylate trans-4-pentylcyclohexyl 2-(trans-4-propylcyclohexyl)-cis-5-cyano-1,3-dioxane-trans-5-carboxylate trans-4-heptylcyclohexyl 2-(trans-4-propylcyclohexyl)-cis-5-cyano-1,3-dioxane-trans-5-carboxylate trans-4-methylcyclohexyl 2-(trans-4-butylcyclohexyl)-cis-5-cyano-1,3-dioxane-trans-5-carboxylate trans-4-ethylcyclohexyl 2-(trans-4-butylcyclohexyl)-cis-5-cyano-1,3-dioxanetrans-5-carboyxylate trans-4-propylcyclohexyl 2-(trans-4-butylcyclohexyl)-cis-5-cyano-1,3-dioxane-trans-5-carboxylate trans-4-butylcyclohexyl 2-(trans-4-butylcyclohexyl)-cis-5-cyano-1,3-dioxane-trans-5-carboxylate trans-4-pentylcyclohexyl 2-(trans-4-butylcyclohexyl)-cis-5-cyano-1,3-dioxane-trans-5-carboxylate trans-4-heptylcyclohexyl 2-(trans-4-butylcyclohexyl)-cis-5-cyano-1,3-dioxane-trans-5-carboxylate trans-4-methylcyclohexyl 2-(trans-4-pentylcyclohexyl)-cis-5-cyano-1,3-dioxane-trans-5-carboxylate trans-4-ethylcyclohexyl 2-(trans-4-pentylcyclohexyl)-cis-5-cyano-1,3-dioxane-trans-5-carboxylate trans-4-propylcyclohexyl 2-(trans-4-pentylcyclohexyl)-cis-5-cyano-1,3-dioxane-trans-5-carboxylate trans-4-butylcyclohexyl 2-(trans-4-pentylcyclohexyl)-cis-5-cyano-1,3-dioxane-trans-5-carboxylate trans-4-pentylcyclohexyl 2-(trans-4-pentylcyclohexyl)-cis-5-cyano-1,3-dioxane-trans-5-carboxylate trans-4-heptylcyclohexyl 2-(trans-4-pentylcyclohexyl)-cis-5-cyano-1,3-dioxane-trans-5-carboxylate The examples which follow relate to liquid-crystalline phases according to the invention.

EXAMPLE A

A liquid-crystalline phase is prepared which consists of 34.0% of r-1-cyano-cis-4-(trans-4-butylcyclohexyl)-1-heptylcyclohexane, 29.0% of r-1-cyano-cis-4-(trans-4-pentylcyclohexyl)-1-pentylcyclohexane, 10.8% of trans,trans-4-propyl-4'-methoxycyclohexylcyclo-hexane 9.7% of trans,trans-4-propyl-4'-ethoxycyclohexylcyclohexane, 3.0% of trans-4-ethylcyclohexyl r-2-(trans-4-pentylcyclohexyl)-c-5-methyl-1,3 -dioxane-t-5-carb 4.8% of trans-4-pentylcyclohexyl trans,trans-4-butylcyclohexylcyclohexane-4'-carboxylate, 4.8% of trans-4-propylcyclohexyl trans,trans-4-propylcyclohexylcyclohexane-4'-carboxylate and 3.9% of trans-4-pentylcyclohexyl trans,trans-4-propylcyclohexylcyclohexane-4'-carboxylate

EXAMPLE B

A liquid-crystalline phase is prepared which consists of 35.0% of r-1-cyano-cis-4-(trans-4-butylcyclohexyl)-1-heptylcyclohexane, 30.0% of trans-4-pentyl-(trans-5-pentyl-cis-5-cyano-1,3-dioxan-2-yl)-cyclohexane, 10.8% of trans,trans-4-propyl-4'-methoxycyclohexylcyclohexane, 9.7% of trans,trans-4-propyl-4'-ethoxycyclohexylcyclohexane, 3.9% of trans-4-propylcyclohexyl transtrans-4-butylcyclohexylcyclohexane-4'-carboxylate, 3.9% of trans-4-pentylcyclohexyl trans,trans-4-butylcyclohexylcyclohexane-4'-carboxylate, 4.8% of trans-4-propylcyclohexyl trans,trans-4-propylcyclohexylcyclohexane-4'-carboxylate and 3.9% of r-1-cyano-cis-4-(trans-4-pentylcyclohexyl)-1-(trans-4-propylcyclohexyl)-cyclohexane.

EXAMPLE C

A liquid-crystalline phase is prepared which consists of
34% of r-1-cyano-cis-4-(trans-4-butylcyclohexyl)-1-heptylcyclohexane,
29% of r-1-cyano-cis-4-(trans-4-pentylcyclohexyl)-1-pentylcyclohexane,
7% of trans,trans-4'-methoxycyclohexyl-4-propylcyclohexane,
5% of r-5-methyl-c-2-pentyl-5-(trans-4-propylcyclohexyl)-1,3-dioxane,
5% of trans,trans-4'-propoxycyclohexyl-4-propylcyclohexane and
20% of 1-(trans-4-propylcyclohexyl)-2-(trans-4-propylcyclohexyl)-ethane

EXAMPLE D

A liquid-crystalline phase is prepared which consists of
10% of r-2-(4-cyanophenyl)-trans-5-heptyl-cis-5-methyl-1,3-dioxane,
2% of 2-p-cyanophenyl-5-butyl-1,3-dioxane,
15% of p-trans-4-propylcyclohexyl-benzonitrile,
9% of trans-4-propylcyclohexyl trans-4-propylcyclohexanecarboxylate,
10% of trans-4-propylcyclohexyl trans-4-pentacyclohexanecarboxylate,
9% of trans,trans-4'-propylcyclohexyl-4-butyryloxycyclohexane,
9% of trans,trans-4'-propylcyclohexyl-4-hexanoyloxycyclohexane,
6% of trans-4-propylcyclohexyl trans,trans-4-propylcyclohexyl-cyclohexane-4'-carboxylate,
6% of trans-4-pentylcyclohexyl trans,trans-4-propylcyclohexyl-cyclohexane-4'-carboxylate,
6% of trans-4-propylcyclohexyl trans,trans-4-butylcyclohexyl-cyclohexane-4'-carboxylate,
5% of trans-4-pentylcyclohexyl trans,trans-4-butylcyclohexyl-cyclohexane-4'-carboxylate,
5% of 4-(trans-4-propylcyclohexyl)-2'-fluoro-4'-(trans-4-propylcyclohexyl)-biphenyl,
4% of 4-(trans-4-pentylcyclohexyl)-2'-fluoro-4'-(trans-4-propylcyclohexyl)-biphenyl and
4% of 4-(trans-4-pentylcyclohexyl)-2'-fluoro-4'-(trans-4-pentylcyclohexyl)-biphenyl.

EXAMPLE E

A liquid-crystalline phase is prepared which consists of 6% of 2-p-cyanophenyl-5-pentyl-4-methyl-1,3-dioxane,
6% of 2-p-cyanophenyl-5-butyl-1,3-dioxane,
10% of p-trans-4-propylcyclohexyl-benzonitrile,
9% of trans-4-propylcyclohexyl trans-4-propylcyclohexanecarboxylate,
10% of trans-4-propylcyclohexyl trans-4-pentylcyclohexanecarboxylate,
12% of trans,trans-4'-propylcyclohexyl-4-butyryloxycyclohexane,
11% of trans,trans-4'-propylcyclohexyl-4-hexanoyloxycyclohexane,
6% of trans-4-propylcyclohexyl trans,trans-4-propylcyclohexyl-cyclohexane-4'-carboxylate,
6% of trans-4-pentylcyclohexyl trans,trans-4-propylcyclohexyl-cyclohexane-4'-carboxylate,
6% of trans-4-propylcyclohexyl trans,trans-4-butylcyclohexyl-cyclohexane-4'-carboxylate,
5% of trans-4-pentylcyclohexyl trans,trans-4-butylcyclohexyl-cyclohexane-4'-carboxylate,
5% of 4-(trans-4-propylcyclohexyl)-2'-fluoro-4'-(trans-4-propylcyclohexyl)-biphenyl,
4% of 4-(trans-4-pentylcyclohexyl)-2'-fluoro-4'-(trans-4-propylcyclohexyl)-biphenyl and
4% of 4-(trans-4-pentylcyclohexyl)-2'-fluoro-4'-(trans-4-pentylcyclohexyl)-biphenyl.

EXAMPLE F

A liquid-crystalline phase is prepared which consists of
6% of 2-p-cyanophenyl-5-propyl-1,3-dioxane,
6% of 2-p-cyanophenyl-5-butyl-1,3-dioxane,
15% of p-trans-4-propylcyclohexyl-benzonitrile,
19% of trans,trans-4'-propylcyclohexyl-4-butyryloxycyclohexane,
18% of trans,trans-4'-propylcyclohexyl-4-hexanoyloxycyclohexane,
6% of trans-4-propylcyclohexyl trans,trans-4-propylcyclohexyl-cyclohexane-4'-carboxylate,
6% of trans-4-pentylcyclohexyl trans,trans-4-propylcyclohexyl-cyclohexane-4'-carboxylate,
6% of trans-4-propylcyclohexyl trans,trans-4-butylcyclohexyl-cyclohexane-4'-carboxylate,
5% of trans-4-pentylcyclohexyl trans,trans-4-butylcyclohexyl-cyclohexane-4'-carboxylate,
5% of 4-(trans-4-propylcyclohexyl)-2'-fluoro-4'-(trans-4-propylcyclohexyl)-biphenyl,
4% of 4-(trans-4-pentylcyclohexyl)-2'-floro-4'-(trans-4-propylcyclohexyl)-biphenyl and
4% of r-2-[4-trans-4-pentylcyclohexyl)-phenyl]-2-methyl-t-5-pentyl-1,3-dioxane.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:
1. A compound of the formula

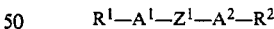

wherein
each of $R^1$ and $R^2$ independently is alkyl of 1–10 C atoms or alkyl of 1–10 C-atoms in which one or two non-adjacent $CH_2$ groups are replaced by O, CO, —OCO—, —COO—, or —CH=CH—, or are F, Cl, Br, CN or $R^3$—$A^3$—$A^2$,
$A^1$ is —A—, —$A^4$—A— or —A—$A^4$,
A is 1,3-dioxane-2,5-diyl or 1,3-dithiane-2,5-diyl each of which is substituted
in the 2-position or 4-position by alkyl of 1–10 C atoms
or in the 5-position by alkyl, alkoxy, fluorinated alkyl or fluorinated alkoxy each of 1–5 C atoms, or by F, Cl, Br or CN,
each of $A^2$, $A^3$ and $A^4$ independently is 1,4-phenylene (Ph), 1,4-phenylene substituted by one or two of F, Cl, $CH_3$ or CN, or 1,4-cyclohexylene Cy, each of $Z^1$ and $Z^2$ independently is —CO—O—, —O—CO—, —CH$_2$CH$_2$—, —OCH$_2$—, —CH$_2$O— or a single bond, and $R^3$ is H, alkyl of 1-10 C atoms or alkyl of 1-10 C atoms in which one or two non-adjacent CH$_2$ groups are replaced by O or —CH=CH—, or is F, Cl, Br or CN.

2. A compound of claim 1 wherein $A^2$, $A^3$ and $A^4$ are Ph or Cy.

3. A compound of claim 1 of the formula $R^1$—A—$A^2$—$R^2$ or $R^1$—A—$Z^1$—$A^2$—$R^2$.

4. A compound of claim 1 of the formula $R^1$—$A^4$—A—$A^2$—$R^2$ $R^1$—A—$A^4$—$A^2$—$R^2$ $R^1$—$A^4$—A—$Z^1$—$A^2$—$R^2$ $R^1$—A—$A^4$—$Z^1$—$A^2$—$R^2$ $R^1$—A—$Z^1$—$A^2$—$A^3$—$R^3$ $R^3$—$A^3$—$Z^2$—A—$Z^1$—$A^2$—$R^2$ or $R^1$—A—$Z^1$—$A^2$—$Z^2$—$A^3$—$R^3$.

5. A compound of claim 1 of the formula $R^1$—$A^4$—A—$A^2$—$A^3$—$R^3$ $R^1$—A—$A^4$—$A^2$—$A^3$—$R^3$ $R^3$—$A^3$—$Z^2$—$A^4$—A—$A^2$—$R^2$ $R^3$—$A^3$—$A^4$—A—$Z^1$—$A^2$—$R^2$ $R^1$—A—$A^4$—$A^2$—$Z^2$—$A^3$—$R^3$ $R^1$—A—$A^4$—$Z^1$—$A^2$—$A^3$—$R^3$ $R^1$—$A^4$—A—$Z^1$—$A^2$—$A^3$—$R^3$ $R^1$—$A^4$—A—$Z^1$—$A^2$—$Z^2$—$A^3$—$R^3$ $R^1$—A—$A^4$—$Z^1$—$A^2$—$Z^2$—$A^3$—$R^3$ ps
$R^3$—$A^3$—$Z^2$—$A^4$—A—$Z^1$—$A^2$—$R^2$, or $R^3$—$A^3$—$Z^2$—A—$A^4$—$Z^1$—$A^2$—$R^2$.

6. A compound of claim 1 of the formula $R^1$—A—Ph—$R^2$ $R^1$—A—Cy—$R^2$.

7. A compound of claim 1 of the formula $R^1$—A—$Z^1$—Ph—$R^2$ $R^1$—A—$Z^1$—Cy—$R^2$ in which $Z^1$ is —CO—O—, —O—CO— or —CH$_2$—CH$_2$—.

8. A compound of claim 1 of the formula $R^1$—Cy—A—Cy—$R^2$ $R^1$—Cy—A—Ph—$R^2$ $R^1$—A—Cy—Cy—$R^2$ $R^1$—A—Ph—Ph—$R^2$ $R^1$—A—Ph—Cy—$R^2$ $R^1$—A—Cy—Ph—$R^2$ 9. A compound of claim 1 of the formula $R^1$—Cy—A—$Z^1$—Cy—$R^2$ $R^1$—Cy—A—$Z^1$—Ph—$R^2$ $R^1$—Ph—A—$Z^1$—Cy—$R^2$ $R^1$—A—Cy—$Z^1$—Cy—$R^2$ $R^1$—A—Ph—$Z^1$—Ph—$R^2$ $R^1$—A—Ph—$Z^1$—Cy—$R^2$ $R^1$—A—Cy—$Z^1$—Ph—$R^2$ $R^1$—A—Z1—Cy—Cy—R3

$R^1$—A—$Z^1$—Ph—Cy—$R^2$ in which $Z^1$ is —CO—O—, —O—CO— or —CH$_2$—CH$_2$—.

10. A compound of claim 1 of the formula $R^1$—Cy—A—Ph—Ph—$R^3$ $R^1$—Cy—A—Ph—Cy—$R^3$ $R^1$—A—Ph—Ph—Cy—$R^3$ $R^1$—A—Ph—Cy—Cy—$R^3$.

11. A compound of claim 1 wherein $R^1$, $R^2$ and $R^3$ are alkyl or alkoxy.

12. A compound of claim 1 wherein $A^2$, $A^3$ and $A^4$ are Cy or Ph.

13. A compound of claim 1 wherein A is

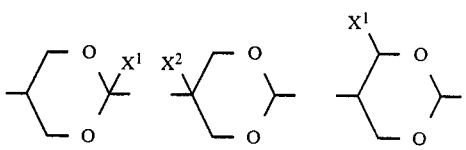

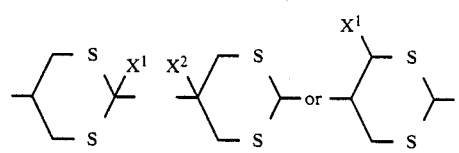

in which $X^1$ is straight-chain alkyl of 1-5 C atoms and $X^2$ is straight-chain alkyl or alkoxy each of 1-5 C atoms, or is F, Cl or CN.

14. A compound of claim 1 of the formula

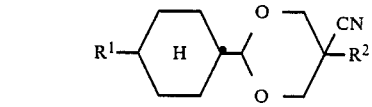

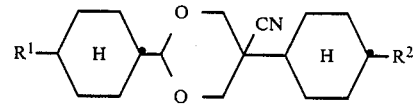

-continued

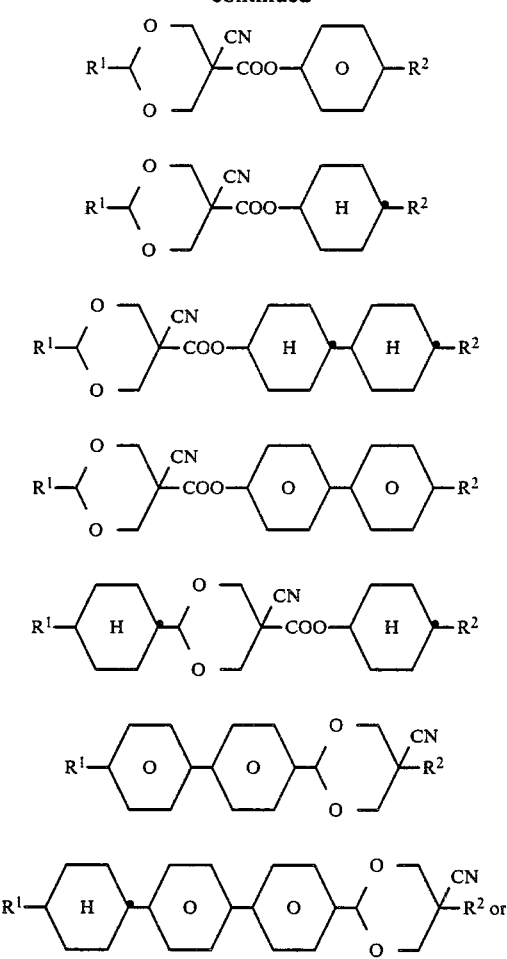
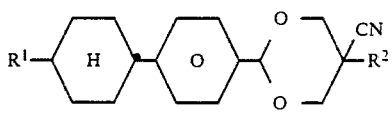

15. A compound of claim 1 wherein $R^1$—, $R^1$—$A^4$— and R —A —Z— or $R^2$—$A^2$—$Z^1$—$A^4$ in the 2- and 5- positions of the ring A are trans relative to one another and have the equatorial position, and the additional substituent on A in the 2- or 5- position has the axial position.

16. A compound of claim 1 wherein A is substituted 1,3-dithiane-2-5-diyl.

17. A compound of claim 1 wherein $A^1$ is —$A^4$—A— or —A—$A^4$—.

18. A compound of claim 1 wherein $R^1$ is $R^3$—$A^3$—$Z^2$.

19. A compound of claim 18, wherein A is substituted 1,3-dioxane-2,5-diyl bonded to $R^1$ in its 2-position.

20. A compound of claim 1 wherein when $R^1$ is attached to substituted 1,3-dioxane-2,5-diyl via the 5-position and is alkyl or alkyl wherein 1 or 2 non-adjacent $CH_2$ groups are replaced by O or —CH=CH— and $Z^1$ is a bond, then (1) when $R^2$ is alkyl or chloro, $A^2$ is not Ph and (2) when $R^2$ is chloro, $A^2$ also is not Ph substituted by chloro.

21. In a liquid-crystalline phase comprising at least two liquid-crystalline compnents, the improvement wherein at least one component is a compound of claim 1.

22. In a liquid crystal display element, comprising a liquid crystal phase, the improvement wherein the phase is one of claim 21.

23. In an electro-optical display element comprising a liquid-crystalline dielectric, the improvement wherein the dielectric is a phase of claim 21.

* * * * *